(12) United States Patent
Bologna et al.

(10) Patent No.: US 6,248,358 B1
(45) Date of Patent: Jun. 19, 2001

(54) BIOADHESIVE PROGRESSIVE HYDRATION TABLETS AND METHODS OF MAKING AND USING THE SAME

(75) Inventors: William J. Bologna, Paris (FR); Howard L. Levine, Oceanside, NY (US); Philippe Cartier; Dominique de Ziegler, both of Paris (FR)

(73) Assignee: Columbia Laboratories, Inc., Rockville Centre, NY (US)

( * ) Notice: Subject to any disclaimer, the term of this patent is extended or adjusted under 35 U.S.C. 154(b) by 0 days.

(21) Appl. No.: 09/379,310

(22) Filed: Aug. 23, 1999

Related U.S. Application Data

(60) Provisional application No. 60/097,843, filed on Aug. 25, 1998.

(51) Int. Cl.[7] .............................. A61K 9/20; A61F 2/00; A61F 6/06; A61F 9/26
(52) U.S. Cl. .......................... 424/465; 424/426; 424/430; 424/464; 424/469; 424/470
(58) Field of Search ................................ 424/426, 430, 424/464, 465, 469, 470

(56) References Cited

U.S. PATENT DOCUMENTS

| 3,133,862 | 5/1964 | Wershaw et al. ...................... 167/81 |
| 4,226,848 | 10/1980 | Nagai et al. ........................... 424/19 |

(List continued on next page.)

FOREIGN PATENT DOCUMENTS

| 0 159 604 A2 | 10/1985 | (EP) . |
| 0 488 139 | 6/1992 | (EP) . |
| 0 654 261 | 5/1995 | (EP) . |
| 0 273 209A | 7/1998 | (EP) . |
| 6-100466 | 4/1994 | (JP) . |

OTHER PUBLICATIONS

Voorspoels, Jody, et al., "Buccal Absorption of Testosterone and Its Esters Using a Bioadhesive Tablet in Dogs," *Pharmaceutical Research*, U.S., New York, NY, vol. 13, No. 8, Aug. 1996, pp. 1228–1232.

PCT International Search Report for PCT/US99/19260, dated Feb. 10, 2000.

Conway, Ann J., et al., "Randomized clinical trial of testosterone replacement therapy in hypogonadal men," *Int'l. J. of Andrology*, 1988, 11, pp. 247–264.

(List continued on next page.)

*Primary Examiner*—Thurman K. Page
*Assistant Examiner*—S. Tran
(74) *Attorney, Agent, or Firm*—Lyon & Lyon LLP

(57) ABSTRACT

A bioadhesive tablet wherein the active ingredient may be protected from water or the surrounding environment, thereby protecting it from metabolism or from other degradation caused by moisture, enzymes, or pH effects, and making it bioavailable only at a controlled rate. The active ingredient may be protected from moisture during the manufacturing process and more importantly may be protected from moisture and the immediate septic environment until after the patient has applied the tablet, and then only at a slow and controlled rate. It is by this process of progressive hydration that the active ingredient remains protected for many hours after administration. It is also by the process of progressive hydration that controlled and sustained release is achieved because only that part of the active ingredient that is the hydrated (aqueous) fraction of the tablet is available for absorption (bioavailable).

25 Claims, 2 Drawing Sheets

U.S. PATENT DOCUMENTS

| | | | |
|---|---|---|---|
| 4,389,393 | 6/1983 | Schor et al. | 424/19 |
| 4,540,566 | 9/1985 | Davis et al. | 424/22 |
| 4,572,832 | 2/1986 | Kigasawa et al. | 424/19 |
| 4,596,795 | 6/1986 | Pitha | 514/58 |
| 4,615,697 | 10/1986 | Robinson | 604/890 |
| 4,740,365 | 4/1988 | Yukimatsu et al. | 424/435 |
| 4,764,378 | 8/1988 | Keith et al. | 424/435 |
| 4,900,552 | 2/1990 | Sanvordeker et al. | 424/422 |
| 4,915,948 | 4/1990 | Gallopo et al. | 424/435 |
| 5,102,666 | 4/1992 | Acharya | 424/487 |
| 5,110,605 | 5/1992 | Acharya | 424/487 |
| 5,252,334 | 10/1993 | Chiang et al. | 424/448 |
| 5,298,017 | 3/1994 | Theeuwes et al. | 604/20 |
| 5,362,498 | 11/1994 | Aiache | 424/435 |
| 5,458,884 | 10/1995 | Britton et al. | 424/435 |
| 5,460,820 | 10/1995 | Ebert et al. | 424/449 |
| 5,554,380 | 9/1996 | Cuca et al. | 424/441 |
| 5,624,677 | 4/1997 | El-Rashidy et al. | 424/435 |
| 5,650,192 | 7/1997 | Britton et al. | 427/2.19 |
| 5,656,284 | 8/1997 | Balkin | 424/435 |
| 5,686,094 | 11/1997 | Acharya | 424/434 |
| 5,750,134 | 5/1998 | Scholz et al. | 424/434 |
| 5,750,136 | 5/1998 | Scholz et al. | 424/448 |
| 5,766,620 | 6/1998 | Heiber et al. | 424/436 |
| 5,780,045 | 7/1998 | McQuinn et al. | 424/434 |
| 5,783,208 | 7/1998 | Venkateshwaran et al. | 424/448 |
| 5,783,212 | 7/1998 | Fassihi et al. | 424/472 |
| 5,800,832 | 9/1998 | Tapolsky et al. | 424/449 |
| 5,804,209 | 9/1998 | De Ponti et al. | 424/434 |
| 5,807,575 | 9/1998 | Dumoulin et al. | 424/464 |
| 5,853,762 | 12/1998 | Myers et al. | 424/488 |
| 5,855,905 | 1/1999 | Oettel et al. | 424/426 |
| 5,958,458 | * 9/1999 | Norling et al. | 424/490 |
| 6,017,521 | * 9/1999 | Robinson et al. | 424/78.02 |

OTHER PUBLICATIONS

Written Opinion (PCT Rule 66) related to International Application No. PCT/US99/19260, dated Jun. 9, 2000.

Patent Abstracts of Japan, Publication No. 06100466, Publication Date Dec. 4. 1994.

J. Voorspoels et al., Buccal Absorption of Testosterone and its Esters Using a Bioadhesive Tablet in Dogs; Pharmaceutical Research, vol. 13, No. 8, 1996; pp. 1228–1232.

Kim et al., Contraception, 1995; 52; pp. 314–316.

Dobs et al., JCE & M, 1998, vol. 83, No. 1; pp. 34–39.

Josef Pitha et al., Hydrophilic Cyclodextrin Derivatives Enable Effective Oral Administration of Steroidal Hormones, Journal of Pharmaceutical Sciences, vol. 75, No. 2, Feb. 1986; pp. 165 and 167.

* cited by examiner

BIOADHESIVE PROGRESSIVE HYDRATION TABLETS AND METHODS OF MAKING AND USING THE SAME

This application claims benefit of Provisional Appln Ser. No. 60/097,843 filed Aug. 25, 1998.

BACKGROUND OF THE INVENTION

1. Field of the Invention

The present invention relates to a bioadhesive, bioerodible tablet for the extended and controlled release of active ingredients. More particularly, the present invention relates to a progressive hydration tablet for adhesion to the wall of a body cavity for the sustained release of active ingredients without premature degradation of the active ingredients caused by metabolism, or by moisture, enzymes or pH effects.

2. Description of the Related Art

Medications and other pharmaceutical products have traditionally been administered in doses via oral ingestion, nasal sprays or injections. These delivery methods have proven ineffective for patients needing a prolonged and constant supply of an active ingredient delivered to the bloodstream. Particularly difficult are patients needing dosing during sleep time hours. For these patients, intravenous venous lines, slow-dissolving pills, and suppositories or transdermal patches have been prescribed. However, the inconvenience and discomfort of IVs, the short life span of many ingested active ingredients from gastrointestinal degradation or first-pass liver metabolism, and the inability of many products to be comfortably delivered transdermally in suitable doses or in controlled concentrations have proven these methods unsatisfactory.

Previous artisans have attempted to meet the needs of the art by developing products for the transmucosal administration of active ingredients. For example, certain active ingredients can be administered quickly into the bloodstream via the walls of a body cavity, such as the buccal or vaginal cavities, without the risk of first pass hepatic degradation. Generally, delivery of active ingredients through mucosal surfaces may be enhanced by the use of bioadhesive formulations. However, one particular area where those in the art have attempted, but heretofore failed, to meet the needs of the art is in developing a bioadhesive tablet useful for sustained release applications without risking degradation of the active ingredient before it is actually released.

"Sustained release" generally refers to continuous or sporadic release of an active ingredient over an extended time after a single administration, whereby the level of active ingredient available to the host patient often is maintained at some constant level over a period of time. As used herein, it is also intended to cover the situation where the release of an active ingredient is controlled over a period at time wherein the level of active ingredient available to the host (bioavailable) may be at a variable but predetermined level at a particular instant in time of treatment.

The sustained release bioadhesive tablets known in the art can be generally broken down into two categories: (1) tablets consisting of water soluble carbomers, and (2) tablets consisting of insoluble polymers. Both types of tablets have proven unsatisfactory for many applications. For example, numerous artisans have attempted to formulate a suitable sustained release bioadhesive tablet from water soluble carbomers, such as carbomer 934P or CARBOPOL™ 974 resin (commercially available from B.F. Goodrich, Cleveland, Ohio). However, such tablets often are only able to adhere to the wall of a body cavity for short periods of time, e.g., six hours or less. Also, these tablets are easily dislodged from the wall of a body cavity and thus place patients using such tablets buccally at risk of asphyxiation. Furthermore, these prior art tablets inherently become hydrated relatively quickly and thus may prematurely expose the reservoir of active ingredient to degradation by moisture or by enzymes from the host environment such as from bacteria in the septic oral or vaginal cavities.

Similarly, tablets comprised of insoluble polymers, such as polycarbophil, have proven unsuitable for many applications. For example, although polycarbophil tablets are capable of prolonged attachment to the wall of a body cavity, such tablets do not adhere immediately, making them impractical for certain treatments such a buccal delivery of active ingredients to patients during sleep time hours. Further, such tablets often do not soften sufficiently to provide comfort and imperceptibility, or provide safety from potential aspiration of the tablet.

Furthermore, for example, neither type of prior art tablet is particularly suitable for treating many conditions. As alluded to previously, there are numerous medical conditions in which a sustained and/or controlled release of active ingredient(s) is desired for any of numerous reasons including, for example, to alleviate the impact of first-pass hepatic metabolism of the active ingredient or the risk of premature degradation of the active ingredient by moisture, pH effects, or enzymes, or to attain the comfort and convenience offered by a suitable bioadhesive tablet. Such conditions include, but are not limited to, for example, those needing treatment with an active ingredient that may be, but is not limited to, a glycoprotein, protein, sex hormone, anti-hormone, nitrate, beta-agonist, beta-antagonist, opioid, opioid-antagonist, antidepressant, HMG CoA (3-hydroxy-3-methylglutaryl Coenzyme A) reductase inhibitor, antihistamine, ACE (angiotensin converting enzyme) inhibitor, and/or prostaglandin. Heretofore the art has required such patents to undergo the more invasive and less suitable techniques and methods of delivery described above.

To illustrate the need in the art, consider hypogonadal men, for example. Hypogonadism in man is characterized by a deficiency or absence of endogenous testosterone production. Abnormally low levels of testosterone may place men at risk of "Andropause", wherein men are at greater risk of cardiovascular disease, Alzheimer's disease, and osteoporosis.

Testosterone has traditionally been used to treat hypogonadal men. However, to be most effective, the treatment must be capable of complete physiologic testosterone replacement. Moreover, the treatment must be capable of providing sustained levels of testosterone through the night, preferably sustaining a peak in the middle of the night. Transdermal testosterone patches typically produce only sub-physiologic levels and thus incomplete relief. Similarly, the prior art buccal tablets hereintofore described would be ineffective or impractical for such sustained testosterone delivery.

The hormone testosterone, like many other drugs, including many other proteins and glycoproteins, undergoes high first pass metabolism. Accordingly, as will be appreciated by one of ordinary skill in the art, buccal or vaginal tablets consisting of materials that are incapable of keeping the interior reservoir of the tablet in the dry state for prolonged periods are inherently incapable of preventing dissolution and swallowing or dissolution and rapid absorption through the muscosa of the active ingredient. Furthermore, as will be appreciated by one of ordinary skill in the art, tablets which are unable to quickly adhere to the target area or are able to become dislodged are impractical for treatments which use night-time delivery, such as testosterone treatment.

Furthermore, as will be appreciated by one of ordinary skill in the art, the advantages of a sustained release, bioadhesive tablet according to the present invention are not limited to the treatment of hypogonadism in men. For example, patients often require sustained release hormone treatment for various conditions. In addition, other medications, such as steroids for treating such conditions as asthma, involve treatments where desired peak levels are at night during sleep-time hours. Accordingly, one of ordinary skill in the art will appreciate that there exists a long-felt, yet unresolved, need to develop a bioadhesive, sustained release tablet to overcome the aforementioned needs of the art, including, but not limited to, the delivery of therapeutically effective amounts of an active ingredient which may be metabolized or otherwise degraded by moisture, enzymes, or pH effects, such as glycoproteins, proteins, sex hormones, anti-hormones, nitrates, beta-agonists, beta-antagonists, opioids, opioid-antagonists antidepressants, HMG CoA reductase inhibitors, antihistamines, ACE inhibitors, and/or prostaglandins.

SUMMARY OF THE INVENTION

The present invention meets the aforementioned needs in the art. Accordingly, it is an object of the invention to provide a bioadhesive tablet that adheres immediately or almost immediately to the target tissue area of a body cavity and generally stays attached substantially throughout treatment. In accordance, with this aspect of the invention, there is provided a bioadhesive tablet that can stay attached and deliver active ingredients in the buccal cavity for as much as eighteen hours or more. In accordance with a related aspect of the invention, there is provided a bioadhesive tablet that can stay attached and deliver active ingredients vaginally for as much as 72 hours or more.

It is another object of the invention to provide a bioadhesive tablet that progressively hydrates, whereby the inner core of the tablet remains protected from moisture and the surrounding environment. In accordance with this aspect of the invention there is provided a bioadhesive tablet suitable for sustained release use in mucosal and other body cavities even with active ingredients comprising proteins or glycoproteins or other treating agents that are particularly susceptible to metabolism, or to enzymatic, pH, or moisture-induced degradation.

It is a related object of the invention to provide a bioadhesive tablet having both controlled and sustained release properties due to a tablet formulation wherein the active ingredient is only progressively made bioavailable over an extended time period by the progressive hydration of the tablet's dry reservoir of active ingredient.

It is another object of the invention to provide a bioadhesive tablet according to the invention that also gelifies and/or swells to help protect a patient using the tablet buccally from asphyxiation, particularly a sleeping patient undergoing treatment.

It is yet another object of the invention to provide methods of making bioadhesive tablets in accordance with the aforementioned objects of the invention. In accordance with one aspect of the invention, there is provided a method of making bioadhesive tablets wherein an active ingredient resistant to premature metabolism and/or degradation is added in the first and/or second step (manufacture of granulate). In accordance with a related aspect of the invention there is provided a method of making bioadhesive tablets wherein an active ingredient prone to premature metabolism and/or degradation is added in the second step (manufacture of the tableting mixture) after the granulate is dried and sieved. Of course, other concerns or factors may affect the choice of which step or steps are appropriate for adding a particular active ingredient.

It is yet another object of the invention to provide methods of using bioadhesive tablets as described herein. In accordance with one aspect of the invention, there is provided a method of using a bioadhesive tablet to administer to a male patient a sustained release of testosterone. In accordance with a related aspect of the invention, there is provided a method of using a bioadhesive tablet to administer to a female patient a sustained release of a hormone, such as testosterone.

The inventors of the present invention have discovered, quite unexpectedly, that these and other objects for the invention may be achieved by making and using tablets comprising an active ingredient, water soluble polymers (e.g., CARBOPOL™ 974P), and insoluble polycarbophil (e.g., NOVEON®, available from B.F. Goodrich Specialty Polymers of Cleveland, Ohio), and preferably hydroxypropylmethyl cellulose (HPMC), lactose, corn starch and other standard tablets ingredients, such as magnesium stearate and talc.

Bioadhesive, progressive hydration tablets according to the invention may be used with any suitable active ingredient and may be used to deliver a therapeutic amount of the active ingredient to a patient at controlled rates for sustained periods of time. Tablets according to the invention may also be constructed in any suitable shape and any suitable size consistent with the intended therapeutic use of the tablet.

Tablets according to the invention may comprise any suitable amount of active ingredient. Suitable amounts of active ingredient according to the invention are may be from minuscule amounts of active ingredient to about 50%, or more, by weight active ingredient. As will be appreciated by one of ordinary skill in the art, "minuscule amounts" is intended to cover those amounts of active ingredient that are disproportionately small relative to the tablet, for example, when only a few micrograms of active ingredient are to be delivered via a tablet weighing over a hundred milligrams. Accordingly, one of ordinary skill in the art will appreciate that any amount of active ingredient, in any ratio, is within the scope of the present invention.

The balance of the tablet according to the invention may comprise water soluble polymer(s) and water insoluble cross-linked polycarboxylic polymer(s). Also, according to the invention, exemplary tablets preferably have between about 1% and about 75% by weight water soluble polymer and between about 0.5% and about 10% by weight water insoluble cross-inked polycarboxylic polymer. In accordance with the invention, such exemplary tablets also preferably include between about 5% and about 50% cellulose. Also in accordance with the invention, presently preferred tablets may have between about 0.5% and about 25% by weight starch. These preferred tablets may also have between about 1% and about 50% by weight lactose.

Furthermore, according to the invention, preferred tablets may comprise from about 0.01% up to about 2% by weight, including about 1% by weight silica; and/or up to about 2% by weight, including about 0.5% to about 2% by weight and up to about 0.5% by weight talc; and/or up to about 2.5% by weight, including about 0.5% to about 2% by weight magnesium stearate.

In one embodiment, said starch is present in about 2% to about 10% by weight, said lactose is present in about 8% to about 16% by weight, said water soluble polymer is present in about 25% to about 35% by weight, and said tablet is adapted for delivering said active ingredient to the bloodstream of a patient via the patient's vaginal cavity.

In another embodiment, said starch is present in about 14% to 24% by weight, said lactose is present in about 17% to about 27% by weight, said water soluble polymer is present in about 5% to about 20% by weight, and said tablet is adapted for delivering said active ingredient to the bloodstream of a patient via the patient's buccal cavity.

In yet another embodiment, the tablet comprises:
an effective amount of an active ingredient,
about 2% to about 30% by weight binder,
about 5% to about 40% by weight lactose,
about 1% to about 3% by weight water insoluble cross-linked polycarboxylic polymer, and
about 5% to about 50% by weight water soluble polymer.

The tablet may further comprise from about 0.2% to about 2% by weight silica; and/or about 0.5% to about 2% by weight talc; and/or about 0.5% to about 2% by weight magnesium stearate.

Accordingly, one of ordinary skill in the art will appreciate that the components of the tablets can be varied to suit a particular purpose. For example, the inventors of the present invention have discovered, quite unexpectedly, that one way of increasing (decreasing) the time it takes a progressive hydration tablet to hydrate is by decreasing (increasing) the amount of lactose and/or starch and increasing (decreasing) the amount of water soluble polymer. Alternatively, the density of the tablet may be altered to affect the hydration period.

Active ingredients suitable for use in the present invention include any active ingredient or ingredients requiring sustained or controlled release, any active ingredient or ingredients requiring extended protection from premature degradation of the active by moisture, pH effects, or enzymes, or any active ingredient requiring administration to a patient with protection from first-pass hepatic metabolism. Exemplary active ingredients suitable for use with the present invention include, but are by no means limited to: (1) glycoproteins, such as follicle-stimulating hormone (FSH), luteinizing hormone (LH), human chorionic gonadotropin (HCG), thryoid-stimulating hormone (TSH) and the like; (2) proteins, such as GnRH (agonist and antagonist), oxytocin analogs, somatostatin analogs, tissue plaminogen activator (TPA), growth hormone releasing hormone (GHRH), corticotropin-releasing hormone analogs (CRH analogs), and the like; (3) sex hormones, such as estradiol, testosterone, progesterone, and the like; (4) anti-hormones, such as tamoxifen, mifepristone, and the like; (5) nitrates, such as nitroglycerin, isosorbide, erythrityl tetranitrate, pentaerythritol tetranitrate, and the like; (6) beta-agonists, such as terbutaline, albuterol, pirbuterol, bitolterol, ritodrine, and the like; (7) beta-antagonists, such as propranolol, metoprolol, nadolol, atenolol, timolol, esmolol, pindolol, acebutolol, labetalol, and the like; (8) opioids, such as morphine, hydromorphone, oxymorphone, codeine, hydrocodone, oxycodone, leverophanol, levallorphan, buprenorphine, fentanyl, nalbuphine, butorphanol, pentazocine, and the like; (9) opioids-antagonists, such as naloxone, nalmefene, and the like; (10) antidepressants, such as amitriptyline, amoxapine, desipramine, doxepin, imipramine, maprotilen, nortriptyline, protripyline, trimipramine, fluoxetine, trazodone, and the like; (11) HMG CoA reductase inhibitors, such as lovastatin, mevastatin, simvastatin, pravastatin, atorvastatin, and the like; (12) antihistamines, such as loratadine, chlorpheniramine maleate, brompheniramine maleate, diphenhydramine, dimenhydrinate, carbinoxamine, promethazine, tripelannamine, and the like; (13) ACE inhibitors, such as captopril, enalapril, lisinopril, and the like; and, (14) prostaglandins, such as misoprostol and the like. A preferred active ingredient is about 1% to about 30% by weight testosterone. Accordingly, one of ordinary skill in the art will appreciate that tablets according to the invention maybe used with a wide variety of active ingredients to treat a wide variety of conditions.

The aforementioned and other aspects of the invention will become more clear by reference to the Figures and descriptions of preferred embodiments.

DESCRIPTION OF THE PREFERRED EMBODIMENTS

Figure 1:
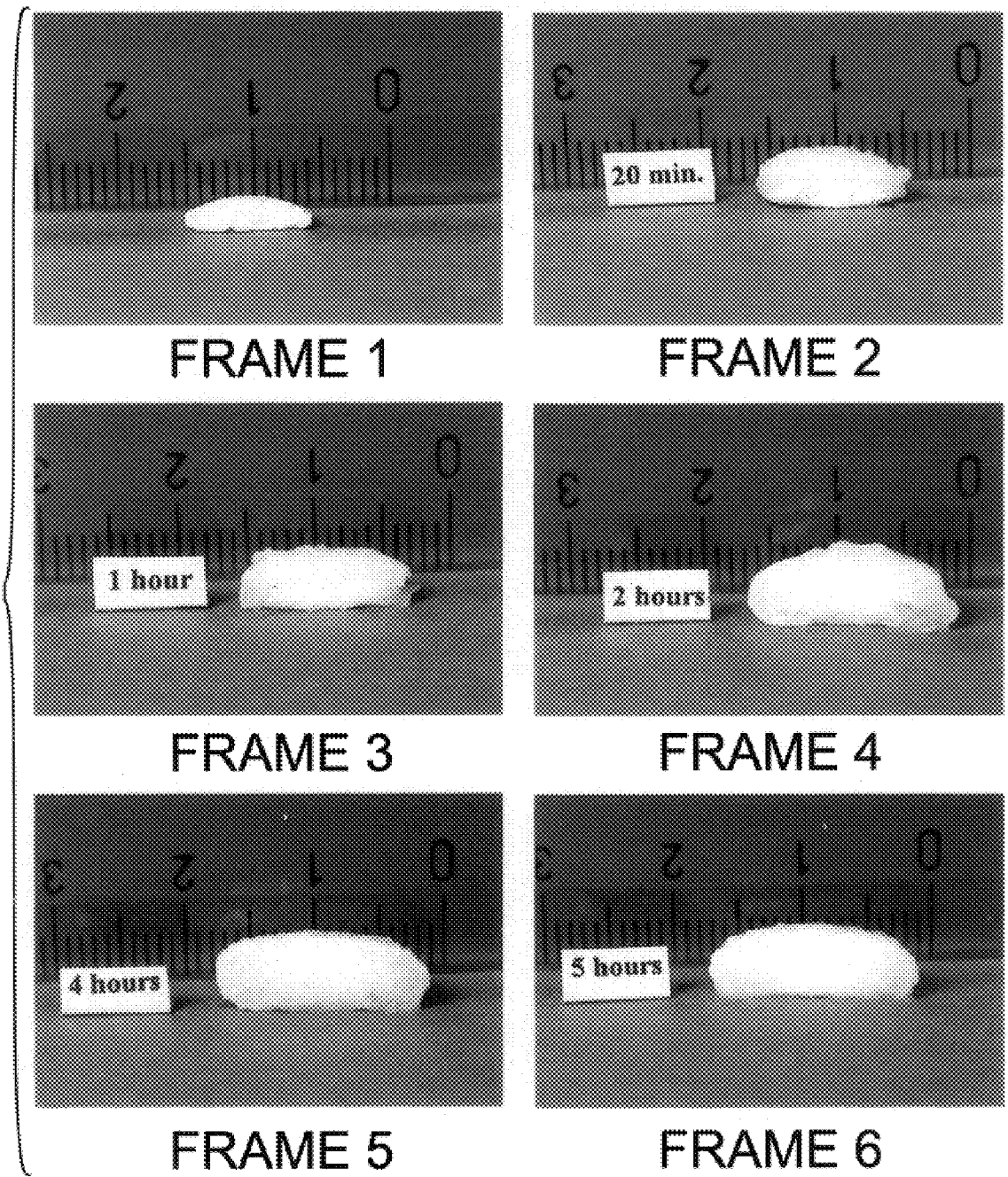
FIG. 1 is a series of photographs depicting the progressive hydration of a bioadhesive tablet according to the invention.

A presently preferred embodiment of the invention is depicted in FIG. 1. As shown in the first-frame of FIG. 1, before the tablet is administered all of the active is in the dry state and thus, not subject to the deleterious action of moisture, pH effects, enzymes or other chemicals. It is also not available for absorption (bioavailable). As shown in frames 2–6 of FIG. 1, over time the residual portion of the active remains in the dry state which both protects it from water and the immediate environment as well as allowing it to serve as a reservoir for the sustained and controlled release of the active. Such a delivery system is well suited for the delivery of proteins, glycoproteins, and other drugs which must be protected from metabolism or during prolonged administration from enzymatic, pH, or moisture-induced degradation.

In a preferred embodiment, when used buccally, progressive hydration of the bioadhesive tablet protects the patient, should the tablet become dislodged, by gelifying and becoming heavier and thus less likely to float in the airway, risking aspiration. This makes this embodiment particularly well suited for agents that should reach their peak levels in the middle of the night, e.g., hormones like testosterone or steroids to treat asthma. According to the invention, the hydration of the tablet can preferably take hours (e.g. 12 to 24 hours) when formulated for buccal tablets or even days when formulated for vaginal use. As will be appreciated by one of ordinary skill in the art, prior art bioadhesive tablets do not protect the active ingredient from moisture, pH, or from enzymes produced by bacteria in the septic oral and vaginal orifices.

Furthermore, as will be appreciated by one of ordinary skill in the art following the teaching of the present application, the tablet can be sized shaped and dosed to meet the needs of the particular treatment being undertaken. For example, the buccal bioadhesive tablet depicted in FIG. 1 was constructed to be only 9 mm in diameter for the comfort of the patient, but made capable of delivering 7 mg of testosterone per day, full physiologic level. By contrast, prior art transdermal patches were only capable of delivering 5 mg per day, in other words a sub-physiologic level.

Figure 2:
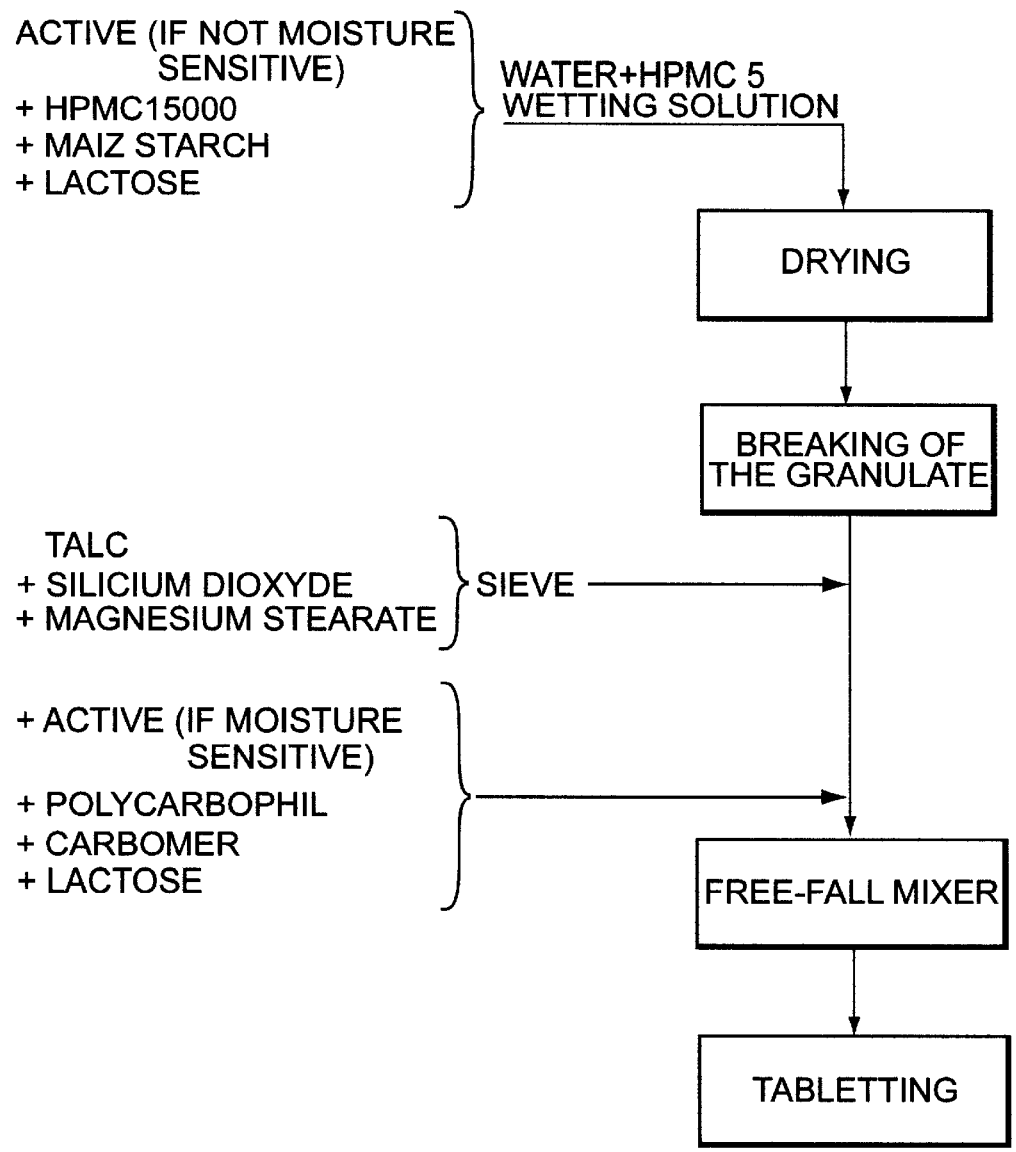
FIG. 2 is a flowchart depicting a presently preferred method of making bioadhesive tablets according to the invention.

A presently preferred method of manufacturing bioadhesive tablets is diagramed in FIG. 2. The presently preferred method involves three steps as described below:

1. First step: manufacture of the granulate.

Hydroxypropylmethyl cellulose 15 000(=HPMC 15 000) is mixed with corn starch and lactose and in case of an active ingredient non sensitive to moisture the active is added. The mixture is wet with an aqueous solution of hydroxypropylmethyl cellulose 5 (=HPMC 5) and knead/granulated.

The granulate is dried in an oven under warm air (50° C.) until moisture content is less than 2.5%

The dried granulate is broken with a stainless steel sieve oscillating granulator mesh size 1000 μm.

2. Second step: manufacture of the tableting mixture. Talc, silicon dioxide magnesium stearate, and in a case of an active sensitive to moisture, the active ingredient is added. All is sieved through a sieving machine having aperture size 500 μm and then transferred into a free-fall mixer.

Addition of the granulate of step 1, followed by polycarbophil, carbomer and lactose. The whole is mixed until homogenous.

3. Third step: tableting

The tableting mixture is compressed into tablets by means of a rotative tableting machine equipped with punches 9 mm flat on the upper side and curved (r=9 mm) on the lower side both with beveled edge. The tablets are dedusted and packed.

As depicted in FIG. 2, an active ingredient that is non-sensitive to moisture is preferably added during the manufacture of the granulate. However, alternatively, the active ingredient can be added during the second step after the granulate is dried and sieved. Also, as will be appreciated by one of ordinary skill in the art, this second method is particularly preferred when the active ingredient is sensitive to moisture.

In a presently preferred manufacturing process, the active ingredient is preferably protected from moisture. A wet granulation is made of lactose, corn starch and HPMC. Testosterone, polycarbophil, carbomer 934P, talc and magnesium stearate are added dry for the final compression.

Furthermore, as will be appreciated by one of ordinary skill in the art following the teaching of the present application, the materials of construction can be varied to optimize the desired characteristics of the tablet. For example, the present inventors have discovered that, quite unexpectedly, by progressively decreasing the amount of lactose and corn starch and progressively increasing the amount of carbomer 934P, the amount of time it takes a tablet to hydrate is progressively increased. Accordingly, as will be appreciated by one of ordinary skill in the art, tablets suited for specific treatments (i.e., specific active, specific dose, specific delivery time) can be manufactured.

These and other aspects of the invention may be more clearly shown by way of example.

EXAMPLE: TESTOSTERONE TABLET

The following is an example of a formulation (Formulation 8, batch #00029906) designed for complete physiologic replacement of testosterone in men:

| Testosterone | 30.000 mg | 24.0% |
|---|---|---|
| HPMC | 26.250 mg | 21.0% |
| Corn Starch | 22.500 mg | 18.0% |
| Monohydrated Lactose | 30.125 mg | 24.1% |
| Silica | 1.250 mg | 1.0% |
| Polycarbophil (Noveon) | 3.125 mg | 2.5% |
| Carbomer 974P | 9.375 mg | 7.5% |
| Talc | 1.500 mg | 1.2% |
| Magnesium stearate | 0.875 mg | 0.7% |

Formulations like the one above produced sustained release in in-vitro dissolution tests. When used in female subjects formulas like this one also produce a sustained and controlled release of testosterone for 12 hours or more.

Table 1 depicts nine different formulations of bioadhesive tablets according to the invention. The active ingredient, testosterone, was held constant at 30.0 mg (24% by weight) so the effect of varying the proportions of the inactive ingredients could be studied.

The testosterone dissolution rates of selected formulations were then studied. Table 2 depicts the testosterone dissolution rate of six tablets selected from Formula 1, batch #0069904. Table 3 depicts the testosterone dissolution rate of six tablets selected from Formula 3, batch #0049904. Table 4 depicts the testosterone dissolution rate of six tablets selected from Formula 5, batch #0029904. Table 5 depicts the testosterone dissolution rate of Formula 6, batch #0019904.

The dissolution rate data was then graphed to illustrate the percent of testosterone released per hour. Chart 1 depicts the testosterone release rate for Formula 1 (see Table 2). Chart 2 depicts the testosterone release rate for Formula 3 (see Table 3). Chart 3 depicts the testosterone release rate for Formula 5 (see Table 4). Chart 4 depicts the testosterone release rate for Formula 6 (see Table 5).

As shown in the charts and tables, by decreasing the amount of lactose and corn starch and increasing the amount of carbomer 934P, the time it takes for the tablet to hydrate is progressively increased. Formulation 1 (0069904) and others like it with high levels of carbomer 934P and low levels of lactose and corn starch are probably best suited for vaginal administration where release is often required over a period days. In the first example given above Formulation 8 (0029906), where the levels of lactose and corn starch are high and carbomer 934P is low, the formula is probably better suited to buccal administration where 12 hours of delivery is usually sufficient.

As will be appreciated by one of ordinary skill in the art, the examples and preferred embodiments are not intended to be limiting, and the invention applies to tablets comprised of any active ingredient and any combination of tablet materials. Furthermore, as will be appreciated by one of ordinary skid in the art, the invention is intended to cover the methods of manufacturing and therapeutic uses of the aforementioned tablets.

What is claimed is:

1. A sustained release, progressive hydration bioadhesive tablet comprising:
    an effective amount of active ingredient selected from the group consisting of glycoproteins, proteins, sex hormones, anti-hormones, nitrates, beta-agonists, beta-antagonists, opioids, opioid-antagonists, antidepressants, HMG CoA reductase inhibitors, antihistamines, ACE inhibitors, prostagladins, and any other active ingredient which is metabolized or degraded by moisture, enzymes or pH, about 5% to about 50% by weight cellulose,
about 0.5% to about 25% by weight starch,
about 1% to about 50% by weight lactose,
about 0.5% to about 10% by weight water insoluble cross-inked polycarboxylic polymer, and
about 1% to about 75% by weight water soluble polymer.

2. The tablet of claim 1, wherein said tablet comprises between a minuscule amount and about 50% by weight active ingredient.

3. The tablet of claim 2, further comprising:
about 1% by weight silica.

4. The tablet of claim 3, further comprising:
about 0.5% to about 2% by weight talc.

5. The tablet of claim 4, further comprising:
about 0.5% to about 1% by weight magnesium stearate.

6. The tablet of claim 5, wherein said starch is present in about 2% to about 10% by weight, said lactose is present in about 8% to 16% by weight, and said water soluble polymer is present in about 25% to about 35% by weight, and wherein said tablet is adapted for delivering said active ingredient to the bloodstream of a patient via the patient's vaginal cavity.

7. The tablet of claim 5, wherein said starch is present in about 14% to 24% by weight, said lactose is present in about 17% to 27% by weight, and said water soluble polymer is present in about 5% to about 20% by weight, and wherein said tablet is adapted for delivering said active ingredient to the bloodstream of a patient via the patient's buccal cavity.

8. A sustained release, progressive hydration bioadhesive tablet comprising:
an effective amount of an active ingredient selected from the group consisting of glycoproteins, proteins, sex hormones, anti-hormones, nitrates, beta-agonists, beta-antagonists, opioids, opioid-antagonists, antidepressants, HMG CoA reductase inhibitors, antihistamines, ACE inhibitors, prostagladins, and any other active ingredient which is metabolized or degraded by moisture, enzymes or pH,
about 2% to about 30% by weight binder,
about 5% to about 40% by weight lactose,
about 1% to about 3% by weight water insoluble cross-linked polycarboxylic polymer, and
about 5% to about 50% by weight water soluble polymer.

9. The tablet of claim 8, further comprising:
about 0.2 to 2% by weight silica.

10. The tablet of claim 9, further comprising:
about 0.5% to about 2% by weight talc.

11. The tablet of claim 10, further comprising:
about 0.5% to about 2% by weight magnesium stearate.

12. The tablet of claim 10, wherein said active ingredient is testosterone and said testosterone is present in an amount of about 1% to about 30% by weight.

13. The tablet of claim 12, wherein said binder is starch and is present in about 2% to about 10% by weight, said lactose is present in about 8% to 16% by weight, said water soluble polymer is present in about 25% to about 35% by weight, and said tablet is adapted for delivering said active ingredient to the bloodstream of a patient via the patient's vaginal cavity.

14. The tablet of claim 12, wherein said starch is present in about 14% to 24% by weight, said lactose is present in about 17% to 27% by weight, said water soluble polymer is present in about 5% to about 20% by weight, and said tablet is adapted for delivering said active ingredient to the bloodstream of a patient via the patient's buccal cavity.

15. A method of delivering an active ingredient to a person comprising administering the active ingredient via a progressive hydration bioadhesive tablet, wherein said tablet comprises an effective amount of the active ingredient selected from the group consisting of glycoproteins, proteins, sex hormones, anti-hormones, nitrates, beta-agonists, beta-antagonists, opioids, opioid-antagonists, antidepressants, HMG CoA reductase inhibitors, antihistamines, ACE inhibitors, prostagladins, and any other active ingredient which is metabolized or degraded by moisture, enzymes or pH, about 1% to about 50% by weight lactose, about 0.5% to about 10% by weight water insoluble cross-linked polycarboxylic polymer, and about 1% to about 75% by weight water soluble polymer.

16. The method of claim 15 wherein the active ingredient is testosterone.

17. A method of treating or preventing ischemia or Alzheimer's disease comprising administering to a patient a sustained release, progressive hydration bioadhesive tablet comprising a therapeutically effective amount of testosterone, about 1% to about 50% by weight lactose, about 0.5% to about 10% by weight water insoluble cross-linked polycarboxylic polymer, and about 1% to about 75% by weight water soluble polymer.

18. The method of claim 17 wherein the bioadhesive tablet is formulated for buccal administration.

19. The method of claim 17, wherein the bioadhesive tablet is formulated for vaginal administration.

20. A sustained release, progressive hydration bioadhesive tablet, comprising a therapeutically effective amount of an active ingredient selected from the group consisting of glycoproteins, proteins, sex hormones, anti-hormones, nitrates, beta-agonists, beta-antagonists, opioids, opioid-antagonists, antidepressants, HMG CoA reductase inhibitors, antihistamines, ACE inhibitors, prostagladins, and any other active ingredient which is metabolized or degraded by moisture, enzymes or pH, about 1% to about 50% by weight lactose, about 0.5% to about 10% by weight water insoluble cross-linked polycarboxylic polymer, and about 1% to about 75% by weight water soluble polymer.

21. A method for preparing a sustained release, progressive hydration bioadhesive tablet, comprising combining an effective amount of an active ingredient selected from the group consisting of glycoproteins, proteins, sex hormones, anti-hormones, nitrates, beta-agonists, beta-antagonists, opioids, opioid-antagonists, antidepressants, HMG CoA reductase inhibitors, antihistamines, ACE inhibitors, prostagladins, and any other active ingredient which is metabolized or degraded by moisture, enzymes or pH together with about 1% to about 50% by weight lactose, about 0.5% to about 10% by weight water insoluble cross-linked polycarboxylic polymer and 1% to about 75% by weight water soluble polymer.

22. The tablet of claim 5, wherein the active ingredient is terbutaline.

23. A The tablet of claim 22, wherein the cellulose is hydroxypropylmethyl cellulose, the starch is corn starch, the insoluble cross-linked polycarboxylic polymer is polycarbophil, the water soluble polymer is carbomer or Carbomer 974P, and the silica is silicon dioxide.

24. The tablet of claim 12, further comprising cellulose.

25. The tablet of claim 24, wherein the cellulose is hydroxypropylmethyl cellulose, the starch is corn starch, the insoluble cross-linked polycarboxylic polymer is polycarbophil, the water soluble polymer is carbomer or Carbomer 974P, and the silica is silicon dioxide.

* * * * *

UNITED STATES PATENT AND TRADEMARK OFFICE
CERTIFICATE OF CORRECTION

PATENT NO. : 6,248,358 B1
DATED : June 19, 2001
INVENTOR(S) : William J. Bologna et al.

It is certified that error appears in the above-identified patent and that said Letters Patent is hereby corrected as shown below:

Column 6,
Line 13, change "maybe" to -- may be --;

Column 8,
After line 36, insert the attached Tables 1-5 and Charts 1-4; and
Line 54, change "skid" to -- skill --;

Column 9,
Line 5, change "cross-inked" to -- cross-linked --.

Signed and Sealed this

Twenty-fourth Day of December, 2002

JAMES E. ROGAN
*Director of the United States Patent and Trademark Office*

Testosterone KT

| | Form. 1 | | Form. 2 | | Form. 3 | | Form. 4 | | Form. 5 | | Form. 6 | | Form. 7 | | Form. 8 | | Form. 9 | |
|---|---|---|---|---|---|---|---|---|---|---|---|---|---|---|---|---|---|---|
| Batch # | 0069904 | | 0059904 | | 0049904 | | 0039904 | | 0029904 | | 0019904 | | 0019906 | | 0029906 | | 0039906 | |
| | mg | % by Weight | mg | % by Weight | mg | % by Weight | mg | % by Weight | mg | % by Weight | mg | % by Weight | mg | % by Weight | mg | % by Weight | mg | % by Weights |
| Testosterone | 30.000 | 24.00 | 30.000 | 24.00 | 30.000 | 24.00 | 30.000 | 24.00 | 30.000 | 24.00 | 30.000 | 24.00 | 30.000 | 24.00 | 30.000 | 24.00 | 30.000 | 24.00 |
| HPMC* 90SH-15000 | 31.250 | 25.00 | 30.000 | 24.00 | 28.750 | 23.00 | 27.500 | 22.00 | 26.250 | 21.00 | 26.250 | 21.00 | 26.250 | 21.00 | 26.250 | 21.00 | 26.250 | 21.00 |
| Cornstarch | 2.500 | 2.00 | 7.500 | 6.00 | 12.500 | 10.00 | 17.500 | 14.00 | 22.500 | 18.00 | 22.500 | 18.00 | 22.500 | 18.00 | 22.500 | 18.00 | 22.500 | 18.00 |
| Monohydrated lactose | 11.375 | 9.10 | 13.875 | 11.10 | 16.375 | 13.10 | 18.875 | 15.10 | 21.375 | 17.10 | 24.500 | 19.60 | 27.625 | 22.10 | 30.125 | 24.10 | 33.250 | 26.60 |
| Silica | 1.250 | 1.00 | 1.250 | 1.00 | 1.250 | 1.00 | 1.250 | 1.00 | 1.250 | 1.00 | 1.250 | 1.00 | 1.250 | 1.00 | 1.250 | 1.00 | 1.250 | 1.00 |
| Polycarbophil acid (Noveon AA) | 3.125 | 2.50 | 3.125 | 2.50 | 3.125 | 2.50 | 3.125 | 2.50 | 3.125 | 2.50 | 3.125 | 2.50 | 3.125 | 2.50 | 3.125 | 2.50 | 3.125 | 2.50 |
| Carbomer 974 P | 43.750 | 35.00 | 37.500 | 30.00 | 31.250 | 25.00 | 25.000 | 20.00 | 18.750 | 15.00 | 15.625 | 12.50 | 12.500 | 10.00 | 9.375 | 7.50 | 6.250 | 5.00 |
| Talc | 0.875 | 0.70 | 0.875 | 0.70 | 0.875 | 0.70 | 0.875 | 0.70 | 0.875 | 0.70 | 0.875 | 0.70 | 0.875 | 0.70 | 1.500 | 1.20 | 1.500 | 1.20 |
| Magnesium stearate | 0.875 | 0.70 | 0.875 | 0.70 | 0.875 | 0.70 | 0.875 | 0.70 | 0.875 | 0.70 | 0.875 | 0.70 | 0.875 | 0.70 | 0.875 | 0.70 | 0.875 | 0.70 |
| Total Weight | 125.000 | 100.00 | 125.000 | 100.00 | 125.000 | 100.00 | 125.000 | 100.00 | 125.000 | 100.00 | 125.000 | 100.00 | 125.000 | 100.00 | 125.000 | 100.00 | 125.000 | 100.00 |

*Hydroxypropylmethyl cellulose*

TABLE 1

TESTOSTERONE DISSOLUTION RATE -- PERCENT DISSOLUTION

BATCH: 0069904 (Formula 1)

DISSOLUTION APPARATUS: ROTATING PADDLE 60 RPM / PLATINUM WIRE SPIRAL

| SAMPLE | WITHDRAW (HOUR) 0 | WITHDRAW (HOUR) 1 | WITHDRAW (HOUR) 2 | WITHDRAW (HOUR) 4 | WITHDRAW (HOUR) 6 | WITHDRAW (HOUR) 8 | WITHDRAW (HOUR) 24 |
|---|---|---|---|---|---|---|---|
| 1 | 0.0 | 0.7 | 1.9 | 7.6 | 10.6 | 16.0 | 83.6 |
| 2 | 0.0 | 0.6 | 1.7 | 6.7 | 11.7 | 18.0 | 88.5 |
| 3 | 0.0 | 0.7 | 2.0 | 6.9 | 11.7 | 17.9 | 84.9 |
| 4 | 0.0 | 0.6 | 1.7 | 7.0 | 11.2 | 17.1 | 88.3 |
| 5 | 0.0 | 0.7 | 1.9 | 6.8 | 10.9 | 17.0 | 87.4 |
| 6 | 0.0 | 0.7 | 2.1 | 6.6 | 12.4 | 18.3 | 86.6 |
| AVERAGE VALUE | 0.0 | 0.7 | 1.9 | 6.9 | 11.4 | 17.4 | 86.6 |

TABLE 2

TESTOSTERONE DISSOLUTION RATE – PERCENT DISSOLUTION

BATCH: 0049904 (Formula 3)

DISSOLUTION APPARATUS: ROTATING PADDLE 60 RPM / PLATINUM WIRE SPIRAL

| SAMPLE | WITHDRAW (HOUR) 0 | WITHDRAW (HOUR) 1 | WITHDRAW (HOUR) 2 | WITHDRAW (HOUR) 4 | WITHDRAW (HOUR) 6 | WITHDRAW (HOUR) 8 | WITHDRAW (HOUR) 24 |
|---|---|---|---|---|---|---|---|
| 1 | 0.0 | 0.9 | 3.1 | 5.6 | 10.6 | 16.5 | 83.6 |
| 2 | 0.0 | 1.1 | 3.1 | 5.6 | 10.5 | 16.9 | 82.2 |
| 3 | 0.0 | 1.2 | 3.4 | 6.3 | 11.8 | 18.0 | 83.4 |
| 4 | 0.0 | 0.9 | 2.9 | 5.4 | 10.8 | 16.7 | 82.7 |
| 5 | 0.0 | 1.1 | 4.9 | 5.7 | 10.6 | 16.7 | 83.0 |
| 6 | 0.0 | 1.0 | 2.9 | 5.6 | 11.0 | 16.8 | 85.6 |
| AVERAGE VALUE | 0.0 | 1.0 | 3.4 | 5.7 | 10.9 | 16.9 | 83.4 |

TABLE 3

TESTOSTERONE DISSOLUTION RATE -- PERCENT DISSOLUTION

BATCH: 0029904  (Formula 5)

DISSOLUTION APPARATUS: ROTATING PADDLE 60 RPM / PLATINUM WIRE SPIRAL

| SAMPLE | WITHDRAW (HOUR) 0 | WITHDRAW (HOUR) 1 | WITHDRAW (HOUR) 2 | WITHDRAW (HOUR) 4 | WITHDRAW (HOUR) 6 | WITHDRAW (HOUR) 8 | WITHDRAW (HOUR) 24 |
|---|---|---|---|---|---|---|---|
| 1 | 0.0 | 0.9 | 2.2 | 5.9 | 10.8 | 16.3 | 80.3 |
| 2 | 0.0 | 0.9 | 2.5 | 6.7 | 11.8 | 17.8 | 87.5 |
| 3 | 0.0 | 0.9 | 2.4 | 6.9 | 12.3 | 17.7 | 75.2 |
| 4 | 0.0 | 0.9 | 2.3 | 6.8 | 12.4 | 18.6 | 82.4 |
| 5 | 0.0 | 0.9 | 2.5 | 6.9 | 12.9 | 19.5 | 83.2 |
| 6 | 0.0 | 0.9 | 2.2 | 6.6 | 12.2 | 18.8 | 86.6 |
| AVERAGE VALUE | 0.0 | 0.9 | 2.4 | 6.6 | 12.1 | 18.1 | 82.5 |

TABLE 4

TESTOSTERONE DISSOLUTION RATE – PERCENT DISSOLUTION

BATCH: 0019904  (Formula 6)

DISSOLUTION APPARATUS: ROTATING PADDLE 60 RPM / PLATINUM WIRE SPIRAL

| SAMPLE | WITHDRAW (HOUR) 0 | WITHDRAW (HOUR) 1 | WITHDRAW (HOUR) 2 | WITHDRAW (HOUR) 4 | WITHDRAW (HOUR) 6 | WITHDRAW (HOUR) 8 | WITHDRAW (HOUR) 24 |
|---|---|---|---|---|---|---|---|
| 1 | 0.0 | 1.2 | 2.1 | 5.9 | 11.1 | 16.1 | 71.7 |
| 2 | 0.0 | 0.8 | 2.0 | 5.0 | 9.7 | 14.1 | 70.1 |
| 3 | 0.0 | 0.9 | 2.3 | 6.4 | 11.3 | 15.8 | 74.6 |
| 4 | 0.0 | 0.9 | 2.0 | 5.5 | 10.4 | 15.0 | 68.6 |
| 5 | 0.0 | 0.8 | 1.8 | 4.9 | 9.9 | 14.6 | 76.6 |
| 6 | 0.0 | 0.9 | 1.8 | 4.9 | 9.1 | 13.1 | 70.3 |
| AVERAGE VALUE | 0.0 | 0.9 | 2.0 | 5.4 | 10.3 | 14.8 | 72.0 |

TABLE 5

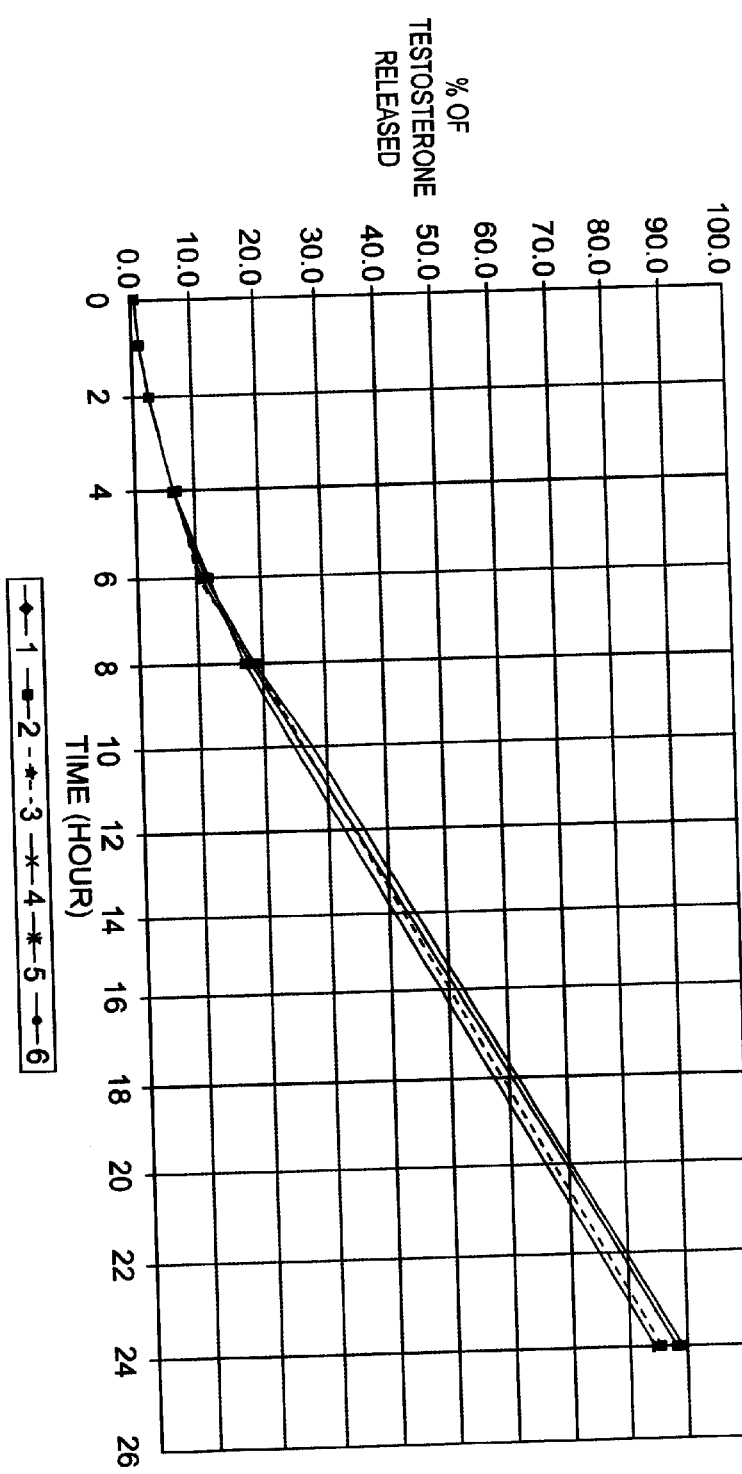

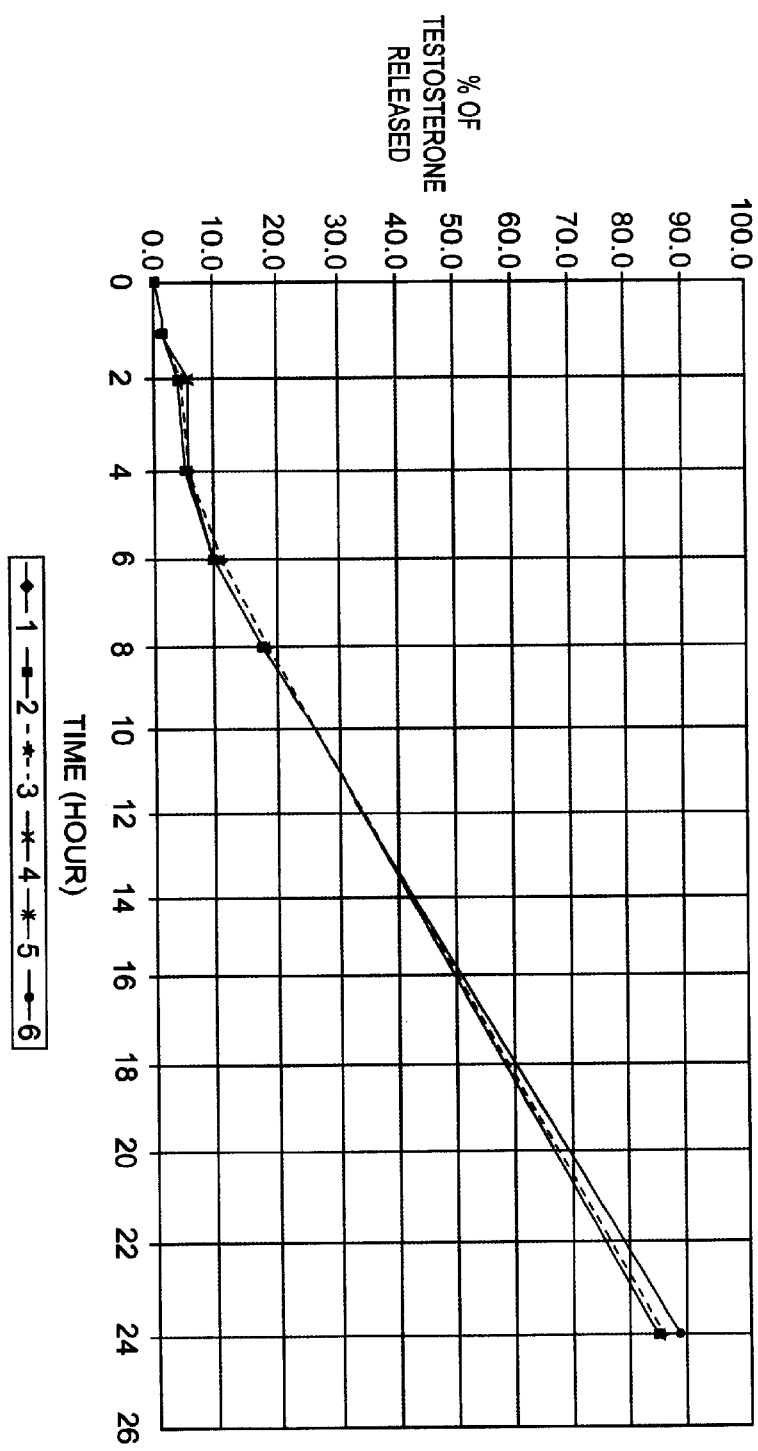
CHART 2

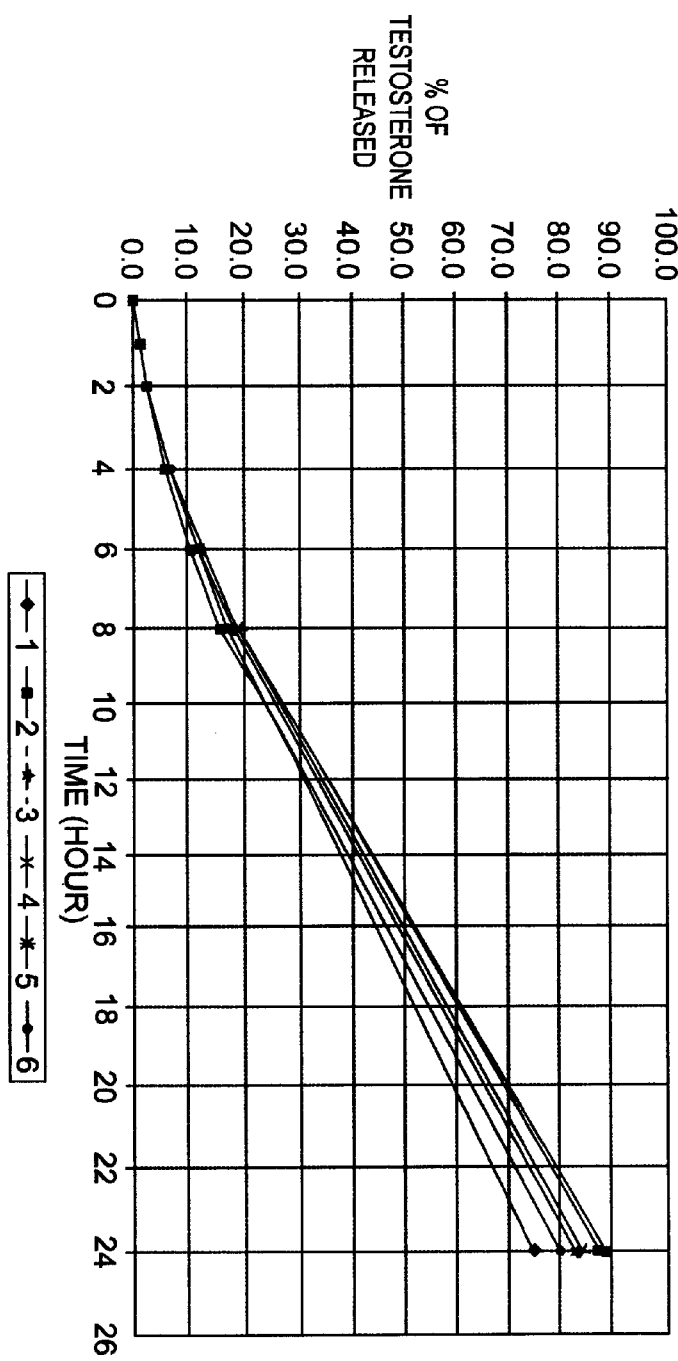

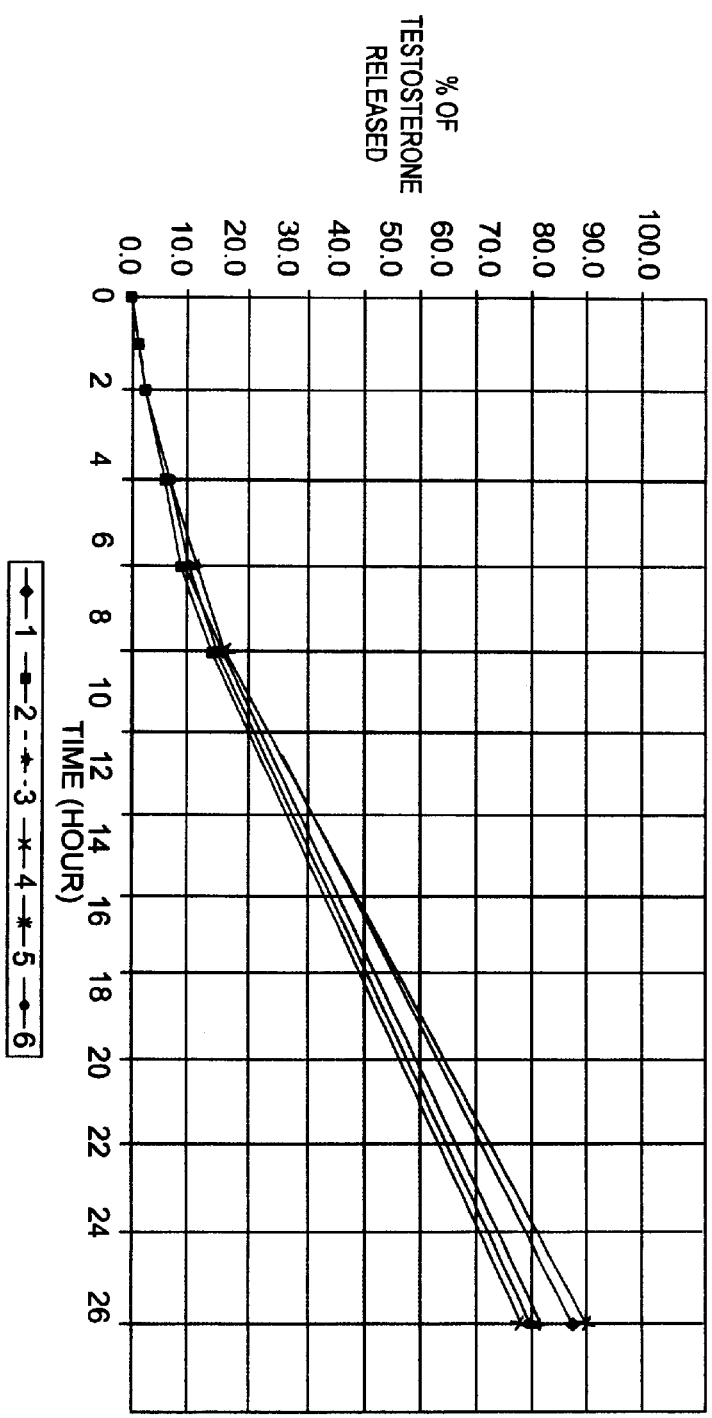

UNITED STATES PATENT AND TRADEMARK OFFICE
CERTIFICATE OF CORRECTION

PATENT NO. : 6,248,358 B1
DATED : June 19, 2001
INVENTOR(S) : William J. Bologna et al.

It is certified that error appears in the above-identified patent and that said Letters Patent is hereby corrected as shown below:

Column 5,
Line 30, delete ", quite unexpectedly,";
Lines 32-33, change "decreasing (increasing)" to -- increasing (decreasing) --; and
Lines 33-34, change "increasing (decreasing)" to -- decreasing (increasing) --;

Column 7,
Lines 51-52, delete ", quite unexpectedly,'"
Line 52, change "decreasing" to -- increasing --;
Line 53, change "increasing" to -- decreasing --; and
Line 54, change "934P" to -- 974P --;

Column 8,
Lines 39, 41 and 46, change "934P" to -- 974P --;
Line 40, change "increased" to -- decreased --;
Lines 42-44, change "for vaginal administration where release is often required over a period days" to -- to buccal administration where 12 hours of delivery is usually sufficient --;
Lines 47-48, change "to buccal administration where 12 hours of delivery is usually sufficient" to -- for vaginal administration where release is often required over a period days --.

Signed and Sealed this

Twenty-sixth Day of August, 2003

JAMES E. ROGAN
*Director of the United States Patent and Trademark Office*